(12) United States Patent
Miyake et al.

(10) Patent No.: US 9,750,255 B2
(45) Date of Patent: Sep. 5, 2017

(54) AGRICULTURAL OR HORTICULTURAL CHEMICAL, METHOD OF CONTROLLING PLANT DISEASES, AND PRODUCT FOR CONTROLLING PLANT DISEASES

(71) Applicant: Kureha Corporation, Tokyo (JP)

(72) Inventors: Taiji Miyake, Tokyo (JP); Nobuyuki Araki, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 15/038,574

(22) PCT Filed: Oct. 8, 2014

(86) PCT No.: PCT/JP2014/076907
§ 371 (c)(1),
(2) Date: May 23, 2016

(87) PCT Pub. No.: WO2015/083438
PCT Pub. Date: Jun. 11, 2015

(65) Prior Publication Data
US 2016/0295865 A1 Oct. 13, 2016

(30) Foreign Application Priority Data
Dec. 5, 2013 (JP) .................................. 2013-252541

(51) Int. Cl.
*A01N 43/653* (2006.01)
*A01N 43/50* (2006.01)
*A01N 43/84* (2006.01)

(52) U.S. Cl.
CPC ........... *A01N 43/653* (2013.01); *A01N 43/50* (2013.01); *A01N 43/84* (2013.01)

(58) Field of Classification Search
CPC ...... A01N 43/653; A01N 43/50; A01N 47/22; A01N 43/40; A01N 37/50; A01N 43/88; A01N 43/54
See application file for complete search history.

(56) References Cited

U.S. PATENT DOCUMENTS

| | | | |
|---|---|---|---|
| 5,028,254 A | 7/1991 | Kumazawa et al. | |
| 2014/0179517 A1* | 6/2014 | Araki | A01N 43/653 504/100 |
| 2014/0315967 A1 | 10/2014 | Araki et al. | |

FOREIGN PATENT DOCUMENTS

| | | |
|---|---|---|
| JP | H01-093574 A | 4/1989 |
| JP | H01-186871 A | 7/1989 |
| WO | WO2012169516 A1 | 12/2012 |
| WO | WO2013077265 A1 | 5/2013 |

OTHER PUBLICATIONS

International Search Report of PCT/JP2014/076907 with mailing date of Jan. 6, 2015.
Extended European Search Report for EP14868350.1, issued on Oct. 26, 2016, 6 pages.
International Preliminary Report on Patentability of PCT/JP2014/076907, mailed on Jun. 16, 2016, 7 pages.
Office Action for Australian Patent Application No. 2014358490, issued on Sep. 7, 2016, 5 pages.
Eurasian Office Action from corresponding application No. 201690802 issued on Nov. 17, 2016, 2 pages
Office Action dated Apr. 26, 2017, with regard to Ukrainian Patent Application No. 201605361, 8 pgs.
Office Action dated Apr. 24, 2017, with regard to Canadian Patent Application No. 2931293, 7 pgs.
Office Action with regard to Eurasian Patent application No. 201690802, dated May 31, 2017 (English language translation attached).

* cited by examiner

*Primary Examiner* — Sudhakar Katakam
(74) *Attorney, Agent, or Firm* — Abel Law Group, LLP

(57) ABSTRACT

An agricultural or horticultural chemical according to the present invention is an agricultural or horticultural chemical containing a plurality of active ingredients, the agricultural or horticultural chemical comprises, as one of the active ingredients, an azole derivative represented by general formula (I), and can be used as a plant disease controlling agent that can reduce the content of an active ingredient:

[Formula 1]

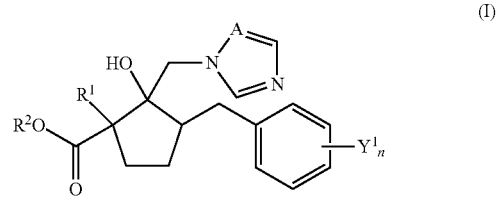

(I)

wherein, $R^1$ represents an alkyl group having from 1 to 6 carbons, $R^2$ represents a hydrogen atom, an alkyl group having from 1 to 3 carbons, an alkenyl group or an alkynyl group having from 2 to 3 carbons, A represents a nitrogen atom or a methine group, $Y^1$ represents a halogen atom, and n represents either 0 or 1.

3 Claims, No Drawings

AGRICULTURAL OR HORTICULTURAL CHEMICAL, METHOD OF CONTROLLING PLANT DISEASES, AND PRODUCT FOR CONTROLLING PLANT DISEASES

TECHNICAL FIELD

The present invention relates to an agricultural or horticultural chemical, a method of controlling plant diseases, and a product for controlling plant diseases. In particular, the present invention relates to an agricultural or horticultural chemical containing at least one type of azole-based compound as an active ingredient, a method of controlling plant diseases using the same, and a product for controlling plant diseases containing the azole-based compound.

BACKGROUND ART

Certain types of 2-substituted-5-benzyl-1-azolyl methyl cyclopentanol derivatives have been known to exhibit fungicidal activity (e.g. refer to Patent Documents 1 to 3).

CITATION LIST

Patent Literature

Patent Document 1: Japanese Unexamined Patent Application Publication No. H01-93574A (published on Apr. 12, 1989)

Patent Document 2: Japanese Unexamined Patent Application Publication No. H01-186871A (published on Jul. 26, 1989)

Patent Document 3: WO/2012/169516 (published on Dec. 13, 2012)

SUMMARY OF INVENTION

Technical Problem

To-date, agricultural and horticultural chemicals having low toxicity toward human and animals and excellent safety in handling, and exhibiting a high controlling effect against a wide variety of plant diseases have been demanded.

Disease control by agricultural and horticultural chemicals has also raised problems such as the effect on non-target organisms, the effect on the environment, and the emergence of chemical-resistant fungi. For that reason, to reduce toxicity in non-target organisms, to reduce environmental load, and to suppress the emergence of chemical-resistant fungi, an agricultural or horticultural chemical that can exhibit a strong controlling effect with a reduced dispersion quantity has been desired.

The present invention has been completed in the light of the above problems. An object of the present invention is to provide an agricultural or horticultural chemical exhibiting an excellent controlling effect and requiring a smaller amount of dispersion to obtain the same degree of effect as that of conventional chemicals.

Solution to Problem

The agricultural or horticultural chemical of the present invention is an agricultural or horticultural chemical containing a plurality of active ingredients, the agricultural or horticultural chemical comprising: as one of the active ingredients, an azole derivative represented by general formula (I) below; and, as another one of the active ingredients, a compound having a cell membrane ergosterol biosynthesis inhibitory capacity.

[Formula 1]

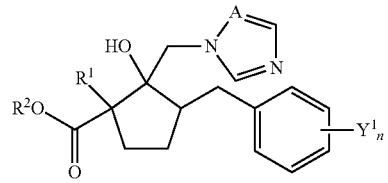

(I)

In formula (I), $R^1$ represents an alkyl group having from 1 to 6 carbons; $R^2$ represents a hydrogen atom, an alkyl group having from 1 to 3 carbons, an alkenyl group having from 2 to 3 carbons, or an alkynyl group having from 2 to 3 carbons; A represents a nitrogen atom or a methine group; $Y^1$ represents a halogen atom; and n represents either 0 or 1.

The product for controlling plant diseases of the present invention has a constitution separately comprising, as a combination preparation by which a plurality of active ingredients are mixed for use: an azole derivative represented by general formula (I) above; and a compound having a cell membrane ergosterol biosynthesis inhibitory capacity.

The method of controlling plant diseases of the present invention comprises a step of performing foliage treatment or non-foliage treatment using the agricultural or horticultural chemical described above.

Advantageous Effects of Invention

Since the agricultural or horticultural chemical of the present invention contains a plurality of compounds as active ingredients, the agricultural or horticultural chemical can exhibit a synergistic effect and can demonstrate a strong controlling effect.

DESCRIPTION OF EMBODIMENTS

An embodiment of the agricultural or horticultural chemical, the product for controlling plant diseases, and the method of controlling plant diseases of the present invention will be described.

Agricultural or Horticultural Chemical

The agricultural or horticultural chemical of the present invention is a mixed formulation and contains a plurality of active ingredients. One of the active ingredients is an azole derivative represented by general formula (I) below. That is, the agricultural or horticultural chemical of the present invention contains at least one other compound as the active ingredient(s) in addition to the azole derivative represented by the general formula (I). The agricultural or horticultural chemical of the present invention contains, as one of the active ingredients, a compound having a cell membrane ergosterol biosynthesis inhibitory capacity in addition to an azole derivative represented by general formula (I).

(1) Active Ingredients (1-1) Azole Derivative

The agricultural or horticultural chemical according to the present invention contains, as one of the active ingredients, an azole derivative represented by general formula (I) below (hereinafter, referred to as azole derivative (I)).

[Formula 2]

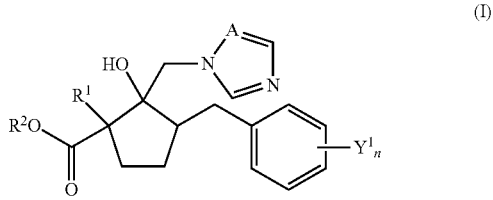

In general formula (I), $R^1$ represents an alkyl group having from 1 to 6 carbons. Examples of the alkyl group having from 1 to 6 carbons include a methyl group, ethyl group, (1-methyl)ethyl group, n-propyl group, 1-methylpropyl group, 2-methylpropyl group, n-butyl group, 1-methylbutyl group, 2-methylbutyl group, 1-ethylpropyl group, 1,1-dimethylethyl group, n-pentyl group, n-hexyl group, and the like. Among these, an alkyl group having from 1 to 4 carbons is preferable as $R^1$, a methyl group and an ethyl group are more preferable, and a methyl group is still more preferable.

In general formula (I), $R^2$ represents a hydrogen atom, an alkyl group having from 1 to 3 carbons, an alkenyl group having from 2 to 3 carbons or an alkynyl group having from 2 to 3 carbons. Examples of the alkyl group having from 1 to 3 carbons include a methyl group, ethyl group, (1-methyl)ethyl group, and n-propyl group. Examples of the alkynyl group having from 2 to 3 carbons include a vinyl group and a 2-propenyl group. An example of the alkynyl group having from 2 to 3 carbons is a 2-propynyl group. Of these, a hydrogen atom, a methyl group, an ethyl group, and an n-propyl group are preferable as $R^2$, and a methyl group is more preferable.

In general formula (I), $Y^1$ represents a halogen atom. More specifically, examples of the halogen atom include a chlorine atom, a fluorine atom, a bromine atom, and an iodine atom. Of these, a chlorine atom and a fluorine atom are preferable as $Y^1$, and a chlorine atom is more preferable.

In general formula (I), n represents either 0 or 1. When n is 1, the bonding position of $Y^1$ is not particularly limited, but a bonding position that forms a 4-substituted benzyl group is preferred.

In general formula (I), A represents a nitrogen atom or a methine group. Among these, a nitrogen atom is preferable as A.

A preferred specific example of the azole derivative (I) is an azole derivative represented by general formula (Ia) below.

[Formula 3]

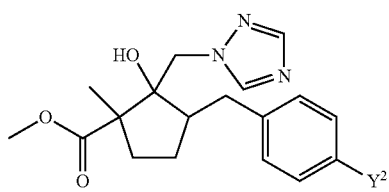

In this instance, in general formula (Ia), $Y^2$ represents a chlorine atom, a fluorine atom, or a hydrogen atom.

Additionally, in the azole derivative (I), there are stereoisomers based on the steric configuration of the organic groups that are bonded to the cyclopentane ring, and there are optical isomers of each stereoisomer. Accordingly, the azole derivative (I) may be either a substance that includes these isomers independently, or a substance that includes an arbitrary ratio of each isomer. Of these, an azole derivative in which the hydroxy group bound to the cyclopentane ring and —$R^1$ are cis-type substances is preferable, and an azole derivative in which the hydroxy group bound to the cyclopentane ring, —$R^1$, and a substituted or unsubstituted benzyl group are cis-type substances is more preferable.

In addition, the agricultural or horticultural chemical may include two or more types of azole derivative (I) in which at least one of $R^1$, $R^2$, A, $Y^1$, and n differs.

The azole derivative (I) exhibits excellent fungicidal activity against many types of fungi that cause plant diseases. Furthermore, the chemical containing the azole derivative (I) as an active ingredient has low toxicity toward human and animals and excellent safety in handling, and can exhibit a high controlling effect against a wide variety of plant diseases.

The method of producing the azole derivative (I) is not particularly limited, and the azole derivative (I) can be produced using a publicly known production method.

(1-2) Compound Having a Cell Membrane Ergosterol Biosynthesis Inhibitory Capacity The agricultural or horticultural chemical of the present invention contains, as one of the active ingredients, a compound having a cell membrane ergosterol biosynthesis inhibitory capacity (called an "ergosterol biosynthesis inhibiting compound" hereafter) in addition to the azole derivative (I). The agricultural or horticultural chemical containing an ergosterol biosynthesis inhibiting compound and the azole derivative (I) as active ingredients can reduce the amount of dispersion of the chemicals required to obtain the same degree of effect as in the case in which an ergosterol biosynthesis inhibiting compound is used alone as a single agent.

Examples of ergosterol biosynthesis inhibiting compounds include azaconazole, bitertanol, bromoconazole, difenoconazole, cyproconazole, diniconazole, fenarimol, fenbuconazole, fenpropidine, fenpropimorph, triazole, flutriafol, hexaconazole, imazalil, imibenconazole, metconazole, ipconazole, myclobutanil, nuarimol, pefurazoate, penconazole, procloraz, propiconazole, prothioconazole, epoxiconazole, simeconazole, spiroxamine, tebuconazole, tetraconazole, triadimefon, triadimenol, triflumizol, triforine, triticonazole, fenhexamid, dodemorph, aldimorph, piperalin, fenhexamid, fenpyrazamine, etaconazole, tridemorph, and the like. Of these, metconazole, prothioconazole, epoxiconazole, propiconazole, ipconazole, tebuconazole, fenpropimorph, and fenpropidine are preferable. An agricultural or horticultural chemical containing at least any one of metconazole, prothioconazole, epoxiconazole, propiconazole, ipconazole, tebuconazole, fenpropimorph, and fenpropidine exhibits particularly high activity. One type of ergosterol biosynthesis inhibiting compound may be contained in the agricultural or horticultural chemical, or a plurality of types of compounds may be contained.

Metconazole, prothioconazole, epoxiconazole, propiconazole, ipconazole, tebuconazole, fenpropimorph, fenpropidine, and other ergosterol biosynthesis inhibiting compounds can be obtained from commercially available formulations or produced using publicly known production methods.

(2) Formulation

In an embodiment of the agricultural or horticultural chemical of the present invention, the mixing ratio of the azole derivative (I) to the ergosterol biosynthesis inhibiting compound (for cases in which a plurality of compounds are used, the total amount thereof) is, in terms of weight ratio, preferably from 1000:1 to 1:1000, more preferably from 750:1 to 1:750, and even more preferably from 500:1 to 1:500. Note that for cases in which a plurality of active ingredients are used as ergosterol biosynthesis inhibiting compounds, the mixing ratio of the plurality of ergosterol biosynthesis inhibiting compounds can be set appropriately depending on the application of the chemicals.

The agricultural or horticultural chemical may contain solid carriers, liquid carriers (diluents), surfactants, or other formulation aids, in addition to the active ingredients described above. Thus, the form of the agricultural or horticultural chemical may take on various forms such as a powder, a wettable powder, granules, or an emulsion.

In the agricultural or horticultural chemical, the total content of the azole derivative (I) and the ergosterol biosynthesis inhibiting compound is preferably from 0.1 to 95 wt. %, more preferably from 0.5 to 90 wt. %, and even more preferably from 2 to 80 wt. % relative to the total amount of the agricultural or horticultural chemical.

Examples of solid carriers that are used as formulation aids include talc, kaolin, bentonite, diatomaceous earth, white carbon, clay, and the like. Examples of liquid carriers that are used as formulation aids include water, xylene, toluene, chlorobenzene, cyclohexane, cyclohexanone, dimethylsulfoxide, dimethylformamide, alcohol, and the like. Surfactants that are used as formulation aids may be used for different purposes depending on their effect. For example, in the case of an emulsifier, polyoxyethylene alkyl aryl ether, polyoxyethylene sorbitan monolaurate, and the like may be used. In the case of a dispersant, lignin sulfonate, dibutyl napthalene sulfonate, and the like may be used. In the case of a wetting agent, alkyl sulfonate, alkyl phenyl sulfonate, and the like may be used.

The agricultural or horticultural chemical may be used in an unmodified state, or may be used after dilution to a predetermined concentration using a diluent such as water. When used after being diluted, the total concentration of the active ingredients is preferably within the range of from 0.001 to 1.0% relative to the total amount of the chemical agent after dilution.

Since the agricultural or horticultural chemical of the present invention exhibits a synergistic effect in its controlling effect against plant diseases, the agricultural or horticultural chemical can reduce the used amount of the compounds required to obtain the same degree of effect as in cases in which the azole derivative (I) or the ergosterol biosynthesis inhibiting compound is used alone as a single agent. For this reason, toxicity in non-target organisms and environmental load can be reduced. In addition, it is anticipated that the emergence of chemical-resistant fungi can be suppressed because the used amount of the respective compounds can be reduced. Furthermore, since the agricultural or horticultural chemical of the present invention contains two ingredients having significantly different molecular structures as the active ingredients for the plant disease controlling effect, the agricultural or horticultural chemical offers a broad spectrum of disease control.

The agricultural or horticultural chemical may be prepared by formulating each of the active ingredients separately and then mixing them to produce a formulated agricultural or horticultural chemical. Therefore, a product for controlling plant diseases separately containing the azole derivative (I) and an ergosterol biosynthesis inhibiting compound as combination preparations by which ingredients are mixed for use in controlling plant diseases, is also included in the scope of the present invention. When two or more ergosterol biosynthesis inhibiting compounds are contained, the two or more ergosterol biosynthesis inhibiting compounds may also be separate from one another.

(3) Plant Disease Controlling Effect

The agricultural or horticultural chemical of the present invention exhibits a controlling effect against a wide range of plant diseases. Examples of applicable diseases include the following. Note that, in the parenthesis after each disease name, major pathogenic fungus(fungi) that causes the disease is(are) indicated.

That is, applicable diseases include soybean rust (*Phakopsora pachyrhizi, Phakopsora meibomiae*), soybean septoria brown spot (*Septoria glycines*), soybean purpura (*Cercospora kikuchii*), rice blast (*Pyricularia grisea*), rice sesame leaf blight (*Cochliobolus miyabeanus*), rice bacterial leaf blight (*Xanthomonas oryzae*), rice sheath blight (*Rhizoctonia solani*), rice stem rot (*Helminthosporium sigmoideun*), rice bakanae disease (*Gibberella fujikuroi*), rice seedling blight (*Pythium aphanidermatum*), barley powdery mildew (*Erysiphe graminis* f. Sp *hordei*), barley stem rust (*Puccinia graminis*), barley yellow rust (*Puccinia striiformis*), barley mottle-leaf (*Pyrenophora graminea*), barley scald (*Rhynchosporium secalis*), barley loose kernel smut (*Ustilago nuda*), barley net blotch (*Pyrenophora teres*), barley *Fusarium* head blight (*Fusarium graminearum, Microdochium nivale*), wheat powdery mildew (*Erysiphe graminis* f. Sp *tritici*), wheat leaf rust (*Puccinia recondita*), wheat yellow rust (*Puccinia striiformis*), wheat eyespot disease (*Pseudocercosporella herpotrichoides*), wheat *Fusarium* head blight (*Fusarium graminearum, Microdochium nivale*), wheat glume blotch (*Phaeosphaeria nodorum*), wheat leaf blight (*Septoria tritici*), wheat pink snow mold (*Microdochium nivale*), wheat damping off (*Gaeumannomyces graminis*), wheat black spot disease (*Epicoccum* spp), wheat macular disease (*Pyrenophora tritici-repentis*), corn smut (*Ustilago maydis*), corn anthracnose (*Colletotrichum graminicola*), corn brown spot disease (*Kabatiella zeae*), corn gray leaf spot (*Cercospora zeae-maydis*), northern leaf blight (*Setosphaeria turcica*), corn northern leaf spot (*Cochliobolus carbonum*), corn leaf spot (*Physoderma maydis*), corn rust (*Puccinia* spp), corn sesame leaf blight (*Bipolaris maydis*), corn yellow sesame leaf blight (*Phyllosticta maydis*), corn *Fusarium* head blight (*Gibberella zeae*), sugarcane rust (*Puccinia* spp), Cucurbitaceae powdery mildew (*Sphaerotheca fuliginea*), anthracnose (*Colletotrichum lagenarium, Glomerella cingulata*), cucumber downy mildew (*Pseudoperonospora cubensis*), cucumber gray plague (*Phytophthora capsici*), cucumber vine wilt (*Fusarium oxysporum* f.sp.*cucumerinum*), watermelon vine wilt (*Fusarium oxysporum* f.sp. *niveum*), apple powdery mildew (*Podosphaera leucotricha*), apple scab (*Venturia inaequalis*), apple monilia disease (*Monilinia mali*), apple leaf spot disease (*Alternaria alternata*), apple franc disease (*Valsa mali*), pear black spot disease (*Alternaria kikuchiana*), pear powdery mildew (*Phyllactinia pyri*), pear chocolate spot (*Gymnosporangium asiaticum*), pear scab (*Venturia nashicola*), strawberry powdery mildew (*Sphaerotheca humuli*), stone fruit orchard brown rot (*Monilinia fructicola*), citrus blue mold (*Penicillium italicum*), grape powdery mildew (*Uncinula necator*), grape downy mildew (*Plasmopara viticola*), grape evening rot (*Glomerella cingulata*), grape rust (*Phakopsora ampelopsidis*), tomato powdery mildew (*Erysiphe cichoracearum*), tomato early blight (*Alternaria solani*), eggplant powdery mildew (*Erysiphe cichoracearum*), potato early blight (*Alternaria* solani), tobacco powdery mildew (*Erysiphe cichoracearum*), tobacco chocolate spot (*Alternaria longipes*), sugar beet brown spot *Cercospora beticola* (*Cercospora beticola*), radish chlorosis (*Fusarium oxysporum* f.sp.*raphani*), gray mold disease that affects a variety of crops (*Botrytis cinerea*) and rot (*Sclerotinia sclerotiorum*), and the like.

In addition, examples of applicable plants include wild plants, cultivars, plants and cultivars bred by conventional hybridizing or plasmogamy, and genetically recombinant plants and cultivars obtained by gene manipulation. Examples of genetically recombined plants and cultivars include herbicide-tolerant crops, pest-resistant crops in which an insecticidal protein-producing gene has been recombined, pathogen-resistant crops in which a pathogen resistance derivative-producing gene has been recombined, taste-improved crops, yield-improved crops, preservation-improved crops, yield-improved crops, and the like. Specific examples of genetically recombined cultivars include the brand names Roundup Ready, Liberty Link, Clearfield, Yieldgard, Herculex, Bollgard, and the like.

In addition, an embodiment of the agricultural or horticultural chemical of the present invention exhibits an effect of increasing the amount of harvest by regulating the growth or an effect of enhancing the quality of a wide variety of crops and garden plants. Examples of these crops include wheats such as wheat, barley, and oat, food crops such as rice, rapeseed, sugar cane, corn, maize, soy bean, pea, peanut, and sugar beet, cabbage, garlic, radish, carrot, apple, pear, citruses such as mandarin orange, orange and lemon, peach, cherry, avocado, mango, papaya, red pepper, cucumber, melon, strawberry, tobacco, tomato, eggplant, lawn, chrysanthemum, azalea, and other decorative plants.

Furthermore, the azole derivative (I) exhibits an excellent effect in protecting materials from a wide variety of harmful microorganisms that erode industrial materials, and can be used as an active ingredient for industrial material protectants. Because of this, an embodiment of the agricultural or horticultural chemical of the present invention can be also used as an industrial material protectant.

(4) Other Active Ingredients

The agricultural or horticultural chemical of the present invention can be used in combination with other known active ingredients (active ingredients contained in fungicides, insecticides, miticides, or herbicides, and plant growth regulating agents) in addition to the active ingredients described above in order to enhance the performance as an agricultural or horticultural chemical.

Plant Disease Controlling Method

The agricultural or horticultural chemical of the present invention can be used not only in foliage treatment such as foliage spraying but also in non-foliage treatment such as seed treatment, soil-drenching treatment, or water surface treatment. Therefore, the method of controlling plant diseases of the present invention comprises a step of performing foliage treatment or non-foliage treatment using the agricultural or horticultural chemical described above. When non-foliage treatment is performed, the amount of labor required can be reduced in comparison to when foliage treatment is performed.

In the case of application by seed treatment, the chemical is deposited on seeds by mixing and stirring a wettable powder and a powder and the like with seeds or immersing seeds in a diluted wettable powder or the like. The total amount of active ingredients used in the case of seed treatment is, for example, from 0.01 to 10,000 g and preferably from 0.1 to 1,000 g per 100 kg of seeds. Seeds that have been treated with the agricultural or horticultural chemical may be used in the same manner as ordinary seeds.

In the case of application by irrigation treatment, a planting hole or the vicinity thereof may be treated with granules or the like at the time of the transplantation of seedling or the like, or seeds or the earth around a plant may be treated with granules, a wettable powder, or the like. The total amount of active ingredients used in the case of irrigation treatment is, for example, from 0.01 to 10,000 g and preferably from 0.1 to 1000 g per 1 $m^2$ of agricultural or horticultural area.

In the case of application by water surface treatment, the water surface of a paddy field may be treated with granules or the like. The total amount of active ingredients used in the case of water surface treatment is, for example, from 0.1 to 10,000 g and preferably from 1 to 1,000 g per 10 a of the paddy field.

The total amount of active ingredients used for foliar spraying is, for example, from 20 to 5,000 g and preferably from 50 to 2,000 g per 1 ha of the agricultural or horticultural area such as a field, a rice paddy, an orchard, or a greenhouse.

Additionally, since the concentration and quantity used differ depending on the form of the agent, time of use, usage method, usage location, target crops and the like, they may be increased or decreased within the above ranges.

SUMMARY

As described above, the agricultural or horticultural chemical of the present invention has a constitution containing a plurality of active ingredients, the agricultural or horticultural chemical comprising: as one of the active ingredients, an azole derivative represented by general formula (I) below; and, as another one of the active ingredients, a compound having a cell membrane ergosterol biosynthesis inhibitory capacity.

[Formula 4]

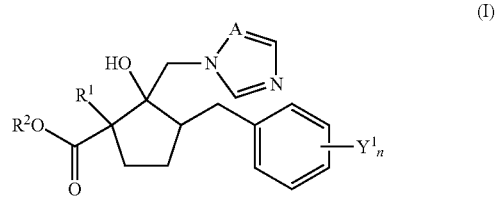

In formula (I), $R^1$ represents an alkyl group having from 1 to 6 carbons; $R^2$ represents a hydrogen atom, an alkyl group having from 1 to 3 carbons, an alkenyl group having from 2 to 3 carbons, or an alkynyl group having from 2 to 3 carbons; A represents a nitrogen atom or a methine group; $Y^1$ represents a halogen atom; and n represents either 0 or 1.

In the agricultural or horticultural chemical of the present invention, the compound having a cell membrane ergosterol biosynthesis inhibitory capacity is preferably at least any one of metconazole, prothioconazole, epoxiconazole, propiconazole, ipconazole, tebuconazole, fenpropimorph, and fenpropidine.

Furthermore, the agricultural or horticultural chemical of the present invention is preferably used as a fungicide.

In addition, in the agricultural or horticultural chemical according to the present invention, it is preferable that the above-mentioned azole derivative be an azole derivative represented by general formula (Ia) below.

[Formula 5]

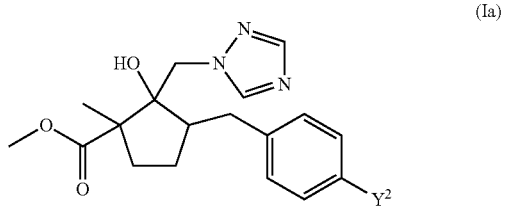

(Ia)

Additionally, in general formula (Ia), $Y^2$ represents a chlorine atom, a fluorine atom or a hydrogen atom.

The product for controlling plant diseases of the present invention has a constitution separately comprising, as a combination preparation by which a plurality of active ingredients are mixed for use: an azole derivative represented by general formula (I) above; and a compound having a cell membrane ergosterol biosynthesis inhibitory capacity.

The method of controlling plant diseases of the present invention comprises a step of performing foliage treatment or non-foliage treatment using the agricultural or horticultural chemical described above.

Embodiments of the present invention will be described in further details hereinafter using working examples. Of course, the present invention is not limited to the examples below, and it goes without saying that various modes are possible with regard to the details thereof. Furthermore, the present invention is not limited to the embodiments described above, and various modifications are possible within the scope indicated in the claims. Embodiments obtained by appropriately combining the technical means disclosed by the embodiments are also included in the technical scope of the present invention. In addition, all of the documents disclosed in the present specification are hereby incorporated by reference.

EXAMPLES

The antimicrobial action of a mixed formulation of methyl 3-(4-chlorobenzyl)-2-hydroxy-1-methyl-2-(1H-1,2, 4-triazole-1-ylmethyl)cyclopentane carbonate (compound (1) hereafter) and a compound having an ergosterol biosynthesis inhibitory capacity was tested.

Test Example 1

In Vitro Antimicrobial Activity Test Using Compound (1) and Prothioconazole

In this test example, the antimicrobial action of a mixed formulation of compound (1) and prothioconazole against *Septoria tritici* was tested.

A plate culture medium containing chemicals was prepared by mixing compound (1) alone, prothioconazole alone, or compound (1) and prothioconazole in a PDA culture medium at a prescribed concentration. Meanwhile, *Septoria tritici* was punched out from the vicinity of a *Septoria tritici* colony that was cultured in advance on another plate culture medium free of the chemicals using a cork borer having a diameter of 4 mm, and inoculated on the PDA plate culture medium in which the chemicals were mixed. After culturing at 25° C. for 14 days, the diameter of the grown colony was measured. The fungal growth inhibition rate was determined by comparing this diameter of the grown colony and the diameter of the colony on the culture medium free of the chemicals, and by using the following formula $R=100(dc-dt)/dc$. Additionally, in the above formula, R represents a fungal growth inhibition rate (%), dc represents the diameter of a colony on an untreated plate, and dt represents the diameter of a colony on a chemical-treated plate. Next, the synergistic effect of the two types of chemicals was determined with a method using the Colby's formula (below):

Inhibition rate when used as a mixture (theoretical value) $=\alpha+((100-\alpha)\times\beta)/100$ Note that, in the formula above, $\alpha$ and $\beta$ respectively represent the inhibition rates of the compounds during single use of the compounds.

The results are shown in Table 1. The growth inhibition rate upon mixing the compound (1) and prothioconazole was greater than the theoretical value calculated from the inhibition rates upon using each of the compounds alone, and it is clear that the compound (1) and prothioconazole exhibited a synergistic effect.

TABLE 1

| Compound (1) ppm | Prothioconazole ppm | Fungal growth inhibition rate (%) | |
|---|---|---|---|
| | | Measured value | Theoretical value |
| 0 | 2.5 | 100 | — |
| 0 | 0.625 | 51 | — |
| 0 | 0.156 | 21 | — |
| 0 | 0.039 | 10 | — |
| 0 | 0.010 | 0 | — |
| 0.005 | 0 | 35 | — |
| 0.005 | 2.5 | 100 | 100 |
| 0.005 | 0.625 | 84 | 68 |
| 0.005 | 0.156 | 63 | 49 |
| 0.005 | 0.039 | 51 | 42 |
| 0.005 | 0.010 | 37 | 35 |

Test Example 2

In Vitro Antimicrobial Activity Test Using Compound (1) and Metconazole

In this test example, the antimicrobial action of a mixed formulation of compound (1) and metconazole against *Septoria tritici* was tested.

Tests and assessments were performed in the same manner as in Test Example 1 with the exception that metconazole was used in place of prothioconazole.

The results are shown in Table 2. The growth inhibition rate upon mixing the compound (1) and metconazole was greater than the theoretical value calculated from the inhibition rates upon using each of the compounds alone, and it is clear that the compound (1) and metconazole exhibited a synergistic effect.

TABLE 2

| Compound (1) ppm | Metconazole ppm | Fungal growth inhibition rate (%) | |
|---|---|---|---|
| | | Measured value | Theoretical value |
| 0 | 2.5 | 98 | — |
| 0 | 0.625 | 56 | — |

TABLE 2-continued

| Compound (1) ppm | Metconazole ppm | Fungal growth inhibition rate (%) | |
|---|---|---|---|
| | | Measured value | Theoretical value |
| 0 | 0.156 | 11 | — |
| 0 | 0.039 | 0 | — |
| 0 | 0.010 | 0 | — |
| 0.02 | 0 | 3 | — |
| 0.02 | 2.5 | 99 | 98 |
| 0.02 | 0.625 | 58 | 57 |
| 0.02 | 0.156 | 30 | 14 |
| 0.02 | 0.039 | 11 | 3 |
| 0.02 | 0.010 | 14 | 3 |

Test Example 3

In Vitro Antimicrobial Activity Test Using Compound (1) and Epoxiconazole

In this test example, the antimicrobial action of a mixed formulation of compound (1) and epoxiconazole against *Fusarium graminearum* was tested.

A plate culture medium containing chemicals was prepared by mixing compound (1) alone, epoxiconazole alone, or compound (1) and epoxiconazole in a PDA culture medium at a prescribed concentration. *Fusarium graminearum* was punched out from the vicinity of a *Fusarium graminearum* colony using a cork borer having a diameter of 4 mm, and inoculated on the PDA plate culture medium in which the chemicals were mixed. After culturing at 25° C. for 3 days, the diameter of the grown colony was measured. The fungal growth inhibition rate was determined in the same manner as in Test Example 1 by comparing this diameter of the grown colony and the diameter of the colony on the culture medium free of the chemicals. In addition, the synergistic effect was determined using a method that used Colby's formula in the same manner as Test Example 1.

The results are shown in Table 3. The growth inhibition rate upon mixing the compound (I) and epoxiconazole was greater than the theoretical value calculated from the inhibition rates upon using each of the compounds alone, and it is clear that the compound (1) and epoxiconazole exhibited a synergistic effect.

TABLE 3

| Compound (1) ppm | Epoxiconazole ppm | Fungal growth inhibition rate (%) | |
|---|---|---|---|
| | | Measured value | Theoretical value |
| 0 | 2.50 | 88 | — |
| 0 | 0.63 | 57 | — |
| 0 | 0.16 | 39 | — |
| 0 | 0.04 | 27 | — |
| 0 | 0.01 | 22 | — |
| 1.25 | 0 | 93 | — |
| 1.25 | 2.50 | 100 | 99 |
| 1.25 | 0.63 | 100 | 97 |
| 1.25 | 0.16 | 98 | 96 |
| 1.25 | 0.04 | 98 | 95 |
| 1.25 | 0.01 | 98 | 95 |

Test Example 4

In Vitro Antimicrobial Activity Test Using Compound (1) and Propiconazole

In this test example, the antimicrobial action of a mixed formulation of compound (1) and propiconazole against *Microdochium nivale* was tested.

A plate culture medium containing chemicals was prepared by mixing compound (1) alone, propiconazole alone, or compound (1) and propiconazole in a PDA culture medium at a prescribed concentration. *Microdochium nivale* was punched out from the vicinity of a *Microdochium nivale* colony that was cultured in advance on another plate culture medium free of the chemicals using a cork borer having a diameter of 4 mm, and inoculated on the PDA plate culture medium in which the chemicals were mixed. After culturing at 25° C. for 3 days, the diameter of the grown colony was measured. The fungal growth inhibition rate was determined in the same manner as in Test Example 1 by comparing this diameter of the grown colony and the diameter of the colony on the culture medium free of the chemicals. In addition, the synergistic effect was determined using a method that used Colby's formula in the same manner as Test Example 1.

The results are shown in Table 4. The growth inhibition rate upon mixing the compound (1) and propiconazole was greater than the theoretical value calculated from the inhibition rates upon using each of the compounds alone, and it is clear that the compound (1) and propiconazole exhibited a synergistic effect.

TABLE 4

| Compound (1) ppm | Propiconazole ppm | Fungal growth inhibition rate (%) | |
|---|---|---|---|
| | | Measured value | Theoretical value |
| 0 | 2.5 | 76 | — |
| 0 | 0.625 | 45 | — |
| 0 | 0.156 | 0 | — |
| 0.313 | 0 | 26 | — |
| 0.313 | 2.5 | 95 | 83 |
| 0.313 | 0.625 | 64 | 59 |
| 0.313 | 0.156 | 39 | 26 |

Test Example 5

In Vitro Antimicrobial Activity Test Using Compound (1) and Tebuconazole

In this test example, the antimicrobial action of a mixed formulation of compound (1) and tebuconazole against *Penicilium italicum* was tested.

A plate culture medium containing chemicals was prepared by mixing compound (1) alone, tebuconazole alone, or compound (1) and tebuconazole in a PDA culture medium at a prescribed concentration. *Penicilium italicum* was punched out from the vicinity of a *Penicilium italicum* colony that was cultured in advance on another plate culture medium free of the chemicals using a cork borer having a diameter of 4 mm, and inoculated on the PDA plate culture medium in which the chemicals were mixed. After culturing at 25° C. for 3 days, the diameter of the grown colony was measured. The fungal growth inhibition rate was determined in the same manner as in Test Example 1 by comparing this diameter of the grown colony and the diameter of the colony on the culture medium free of the chemicals. In addition, the synergistic effect was determined using a method that used Colby's formula in the same manner as Test Example 1.

The results are shown in Table 5. The growth inhibition rate upon mixing the compound (1) and tebuconazole was greater than the theoretical value calculated from the inhibition rates upon using each of the compounds alone, and it is clear that the compound (1) and tebuconazole exhibited a synergistic effect.

TABLE 5

| Compound (1) ppm | Tebuconazole ppm | Fungal growth inhibition rate (%) | |
|---|---|---|---|
| | | Measured value | Theoretical value |
| 0 | 10.00 | 100 | — |
| 0 | 2.50 | 87 | — |
| 0 | 0.63 | 68 | — |
| 0 | 0.16 | 30 | — |
| 0 | 0.04 | 3 | — |
| 1.25 | 0 | 83 | — |
| 1.25 | 10.00 | 100 | 100 |
| 1.25 | 2.50 | 100 | 98 |
| 1.25 | 0.63 | 100 | 94 |
| 1.25 | 0.16 | 98 | 88 |
| 1.25 | 0.04 | 98 | 83 |

Test Example 6

In Vitro Antimicrobial Activity Test Using Compound (1) and Ipconazole

In this test example, the antimicrobial action of a mixed formulation of compound (1) and ipconazole against *Phaeosphaeria nodorum* was tested.

A plate culture medium containing chemicals was prepared by mixing compound (1) alone, ipconazole alone, or compound (1) and ipconazole in a PDA culture medium at a prescribed concentration. *Phaeosphaeria nodorum* was punched out from the vicinity of a *Phaeosphaeria nodorum* colony that was cultured in advance on another plate culture medium free of the chemicals using a cork borer having a diameter of 4 mm, and inoculated on the PDA plate culture medium in which the chemicals were mixed. After culturing at 25° C. for seven days, the diameter of the grown colony was measured. The fungal growth inhibition rate was determined in the same manner as in Test Example 1 by comparing this diameter of the grown colony and the diameter of the colony on the culture medium free of the chemicals. In addition, the synergistic effect was determined using a method that used Colby's formula in the same manner as Test Example 1.

The results are shown in Table 6. The growth inhibition rate upon mixing the compound (1) and ipconazole was greater than the theoretical value calculated from the inhibition rates upon using each of the compounds alone, and it is clear that the compound (1) and ipconazole exhibited a synergistic effect.

TABLE 6

| Compound (1) ppm | Ipconazole ppm | Fungal growth inhibition rate (%) | |
|---|---|---|---|
| | | Measured value | Theoretical value |
| 0 | 0.63 | 76 | — |
| 0 | 0.16 | 62 | — |
| 0 | 0.04 | 31 | — |
| 0 | 0.01 | 20 | — |
| 1.25 | 0 | 89 | — |
| 1.25 | 0.63 | 100 | 97 |
| 1.25 | 0.16 | 100 | 96 |
| 1.25 | 0.04 | 100 | 92 |
| 1.25 | 0.01 | 100 | 91 |

Test Example 7

In Vitro Antimicrobial Activity Test Using Compound (1) and Fenpropimorph

In this test example, the antimicrobial action of a mixed formulation of compound (1) and fenpropimorph against *Septoria tritici* was tested.

A plate culture medium containing chemicals was prepared by mixing compound (1) alone, fenpropimorph alone, or compound (1) and fenpropimorph in a PDA culture medium at a prescribed concentration. Meanwhile, *Septoria tritici* was punched out from the vicinity of a *Septoria tritici* colony that was cultured in advance on another plate culture medium free of the chemicals using a cork borer having a diameter of 4 mm, and inoculated on the PDA plate culture medium in which the chemicals were mixed. After culturing at 25° C. for 14 days, the diameter of the grown colonies were measured, and the fungal growth inhibition rate was determined by comparing the diameter with the diameter of a colony on the culture medium that did not include the chemicals in the same manner as Test Example 1. In addition, the synergistic effect was determined using a method that used Colby's formula in the same manner as Test Example 1.

The results are shown in Table 7. The growth inhibition rate upon mixing the compound (1) and fenpropimorph was greater than the theoretical value calculated from the inhibition rates upon using each of the compounds alone, and it is clear that the compound (1) and fenpropimorph exhibited a synergistic effect.

TABLE 7

| Compound (1) ppm | Fenpropimorph ppm | Fungal growth inhibition rate (%) | |
|---|---|---|---|
| | | Measured value | Theoretical value |
| 0 | 10.00 | 45 | — |
| 0 | 2.50 | 42 | — |
| 0 | 0.63 | 23 | — |
| 0 | 0.16 | 21 | — |
| 0 | 0.04 | 16 | — |
| 1.25 | 0 | 70 | — |
| 1.25 | 10.00 | 91 | 84 |
| 1.25 | 2.50 | 91 | 83 |
| 1.25 | 0.63 | 91 | 77 |
| 1.25 | 0.16 | 83 | 77 |
| 1.25 | 0.04 | 80 | 75 |

Test Example 8

In Vitro Antimicrobial Activity Test Using Compound (1) and Fenpropidine

In this test example, the antimicrobial action of a mixed formulation of compound (1) and fenpropidine against *Septoria tritici* was tested.

Tests and assessments were performed in the same manner as in Test Example 7 with the exception that fenpropidine was used in place of fenpropimorph.

The results are shown in Table 8. The growth inhibition rate upon mixing the compound (1) and fenpropidine was greater than the theoretical value calculated from the inhibition rates upon using each of the compounds alone, and it is clear that the compound (1) and fenpropidine exhibited a synergistic effect.

TABLE 8

| Compound (1) ppm | Fenpropidine ppm | Fungal growth inhibition rate (%) | |
|---|---|---|---|
| | | Measured value | Theoretical value |
| 0 | 10.00 | 40 | — |
| 0 | 2.50 | 38 | — |
| 0 | 0.63 | 40 | — |
| 0 | 0.16 | 0 | — |
| 0 | 0.04 | 0 | — |
| 1.25 | 0 | 77 | — |
| 1.25 | 10.00 | 100 | 86 |
| 1.25 | 2.50 | 90 | 86 |
| 1.25 | 0.63 | 93 | 86 |
| 1.25 | 0.16 | 88 | 77 |
| 1.25 | 0.04 | 82 | 77 |

INDUSTRIAL APPLICABILITY

The present invention can be suitably used as an active ingredient of controlling agents that can control plant diseases while minimizing harmful effects to the plants.

The invention claimed is:

1. A fungicide containing a plurality of active ingredients, in an effective amount of an azole derivative have the general formula 1; and a compound having a cell membrane ergosynthesis inhibitor capacity:

[Formula 1]

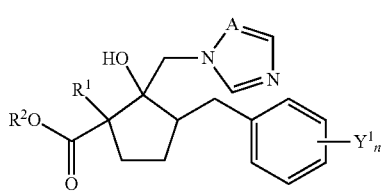

(I)

wherein, $R^1$ represents an alkyl group having from 1 to 6 carbons, $R^2$ represents a hydrogen atom, an alkyl group having from 1 to 3 carbons, an alkenyl group having from 2 to 3 carbons or an alkynyl group having from 2 to 3 carbons, A represents a nitrogen atom, $Y^1$ represents a halogen atom, and n represents either 0 or 1 wherein the compound having a cell membrane ergosterol biosynthesis inhibitory capacity is at least any one of metconazole, prothioconazole, epoxyconazole, propiconazole, ipconazole, tebuconazole, fenpropimorph, and fenpropidine.

2. The agricultural or horticultural chemical according to claim 1, wherein the azole derivative is an azole derivative having the general formula (Ia):

[Formula 2]

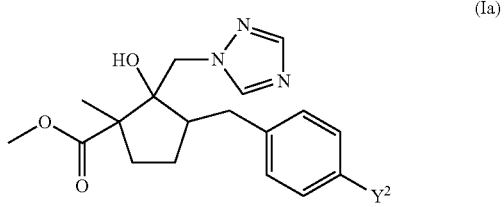

(Ia)

wherein, $Y^2$ is a chlorine atom, a fluorine atom or a hydrogen atom.

3. A product for controlling plant diseases separately comprising, as a combination preparation by which a plurality of active ingredients in an effective amounts are mixed for use: comprising an azole derivative having the general formula (I); and a compound having a cell membrane ergosterol biosynthesis inhibitory capacity:

[Formula 3]

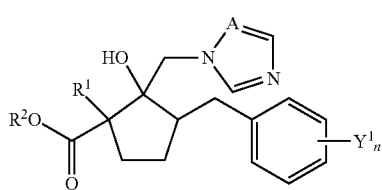

(I)

wherein, $R^1$ represents an alkyl group having from 1 to 6 carbons, R2 represents a hydrogen atom, an alkyl group having from 1 to 3 carbons, an alkenyl group having from 2 to 3 carbons or an alkynyl group having from 2 to 3 carbons, A represents a nitrogen atom, $Y^1$ represents a halogen atom, and n represents either 0 or 1 wherein the compound having a cell membrane ergosterol biosynthesis inhibitory capacity is at least any one of metconazole, prothioconazole, epoxyconazole, propiconazole, ipconazole, tebuconazole, fenpropimorph, and fenpropidine.

* * * * *